United States Patent
Rogers

[11] Patent Number: 5,984,680
[45] Date of Patent: *Nov. 16, 1999

[54] ANTI-ROTATIONAL CONNECTING MECHANISM

[75] Inventor: Dan Paul Rogers, Royal Palm Beach, Fla.

[73] Assignee: Implant Innovations, Inc., Palm Beach Gardens, Fla.

[*] Notice: This patent is subject to a terminal disclaimer.

[21] Appl. No.: 08/952,711

[22] PCT Filed: May 22, 1996

[86] PCT No.: PCT/US96/07427

§ 371 Date: Nov. 19, 1997

§ 102(e) Date: Nov. 19, 1997

[87] PCT Pub. No.: WO96/37161

PCT Pub. Date: Nov. 28, 1996

Related U.S. Application Data

[63] Continuation-in-part of application No. 08/451,083, May 25, 1995, Pat. No. 5,725,375
[60] Provisional application No. 60/002,741, Aug. 24, 1995.

[51] Int. Cl.⁶ .................................................. A61C 8/00
[52] U.S. Cl. .................................... 433/173; 433/172
[58] Field of Search .................... 433/172, 173, 433/174, 175, 176; 403/359, 361; 279/102, 103, 104, 105, 906

[56] References Cited

U.S. PATENT DOCUMENTS

| | | |
|---|---|---|
| 3,958,471 | 5/1976 | Muller . |
| 4,011,602 | 3/1977 | Rybicki et al. . |
| 5,104,318 | 4/1992 | Piche et al. ........................ 433/174 |
| 5,122,059 | 6/1992 | Durr et al. ........................ 433/173 |
| 5,195,892 | 3/1993 | Gersberg .......................... 433/174 |
| 5,197,881 | 3/1993 | Chalifoux ......................... 433/173 |
| 5,295,423 | 3/1994 | Mikic ................................ 81/438 |
| 5,334,024 | 8/1994 | Niznick ............................. 433/173 |
| 5,362,234 | 11/1994 | Salazar et al. .................... 433/169 |
| 5,362,235 | 11/1994 | Daftary ............................ 433/172 |
| 5,417,570 | 5/1995 | Zuest et al. ...................... 433/177 |
| 5,433,606 | 7/1995 | Niznick et al. .................. 433/173 |
| 5,437,551 | 8/1995 | Chalifoux ........................ 433/173 |
| 5,725,375 | 3/1998 | Rogers ............................. 433/172 |

FOREIGN PATENT DOCUMENTS

| | | | |
|---|---|---|---|
| 4 028 855 | 3/1992 | Germany | 433/173 |

*Primary Examiner*—John J. Wilson
*Attorney, Agent, or Firm*—Arnold White & Durkee

[57] ABSTRACT

A dental implant system for providing a progressively tightening anti-rotational connection between a post and a socket. Engagement means on the post and/or socket provide for a small degree of relative rotation between the post and socket upon initial connection, then a progressively tightening connection upon further penetration of the post into the socket and then a final connection which substantially eliminates the relative rotation between the post and socket.

28 Claims, 9 Drawing Sheets

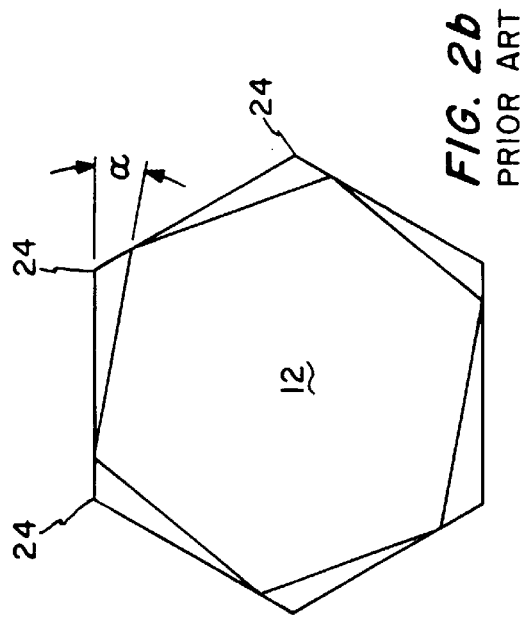
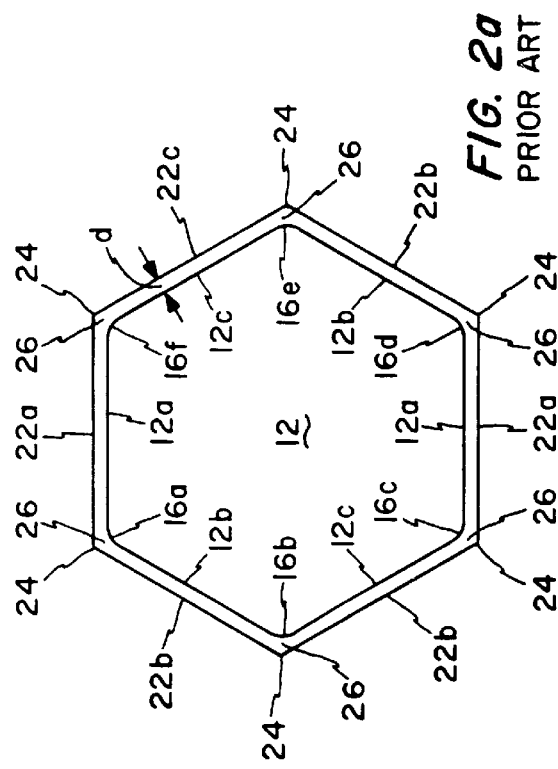
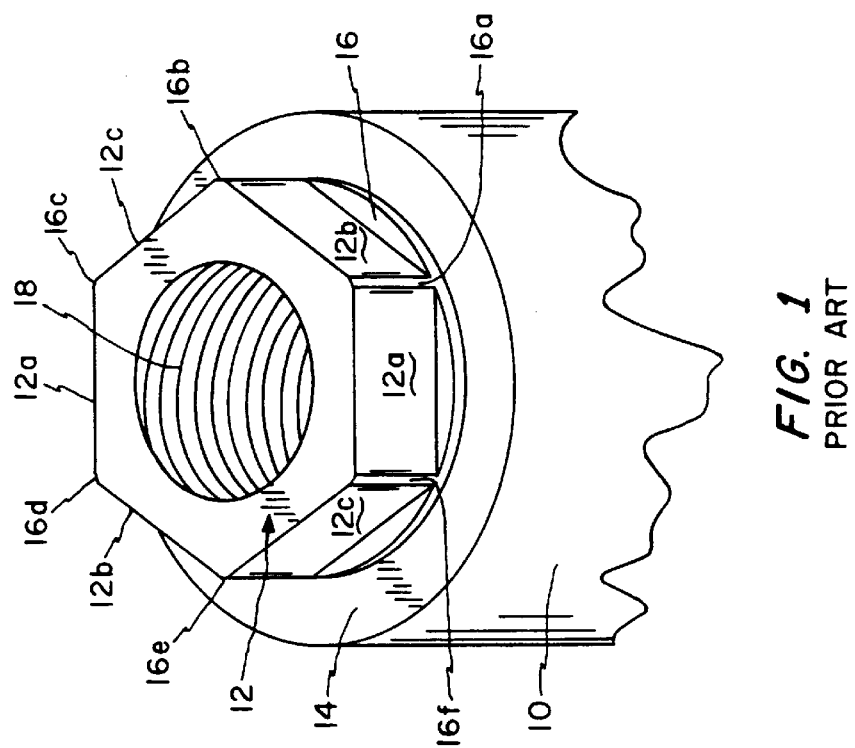

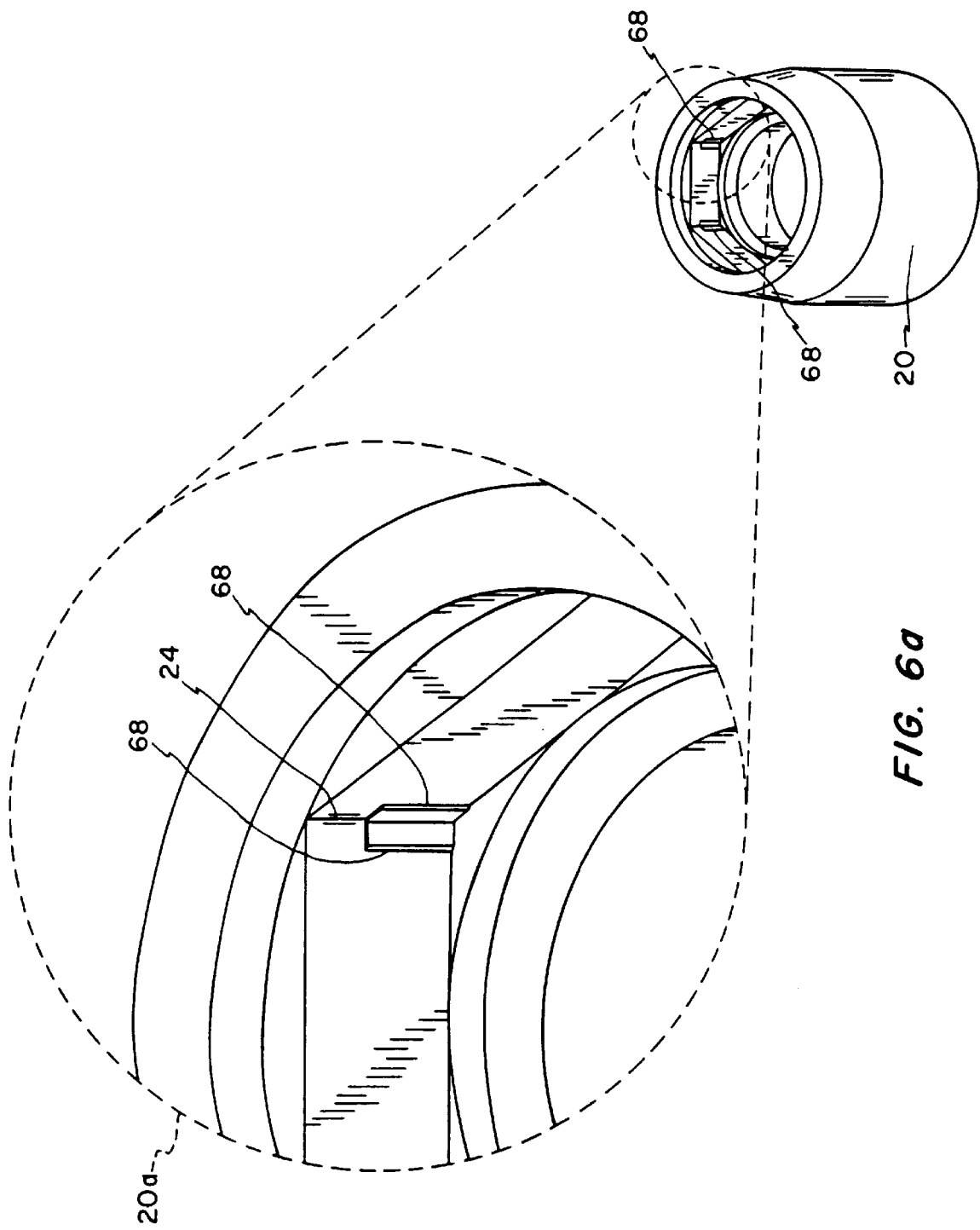

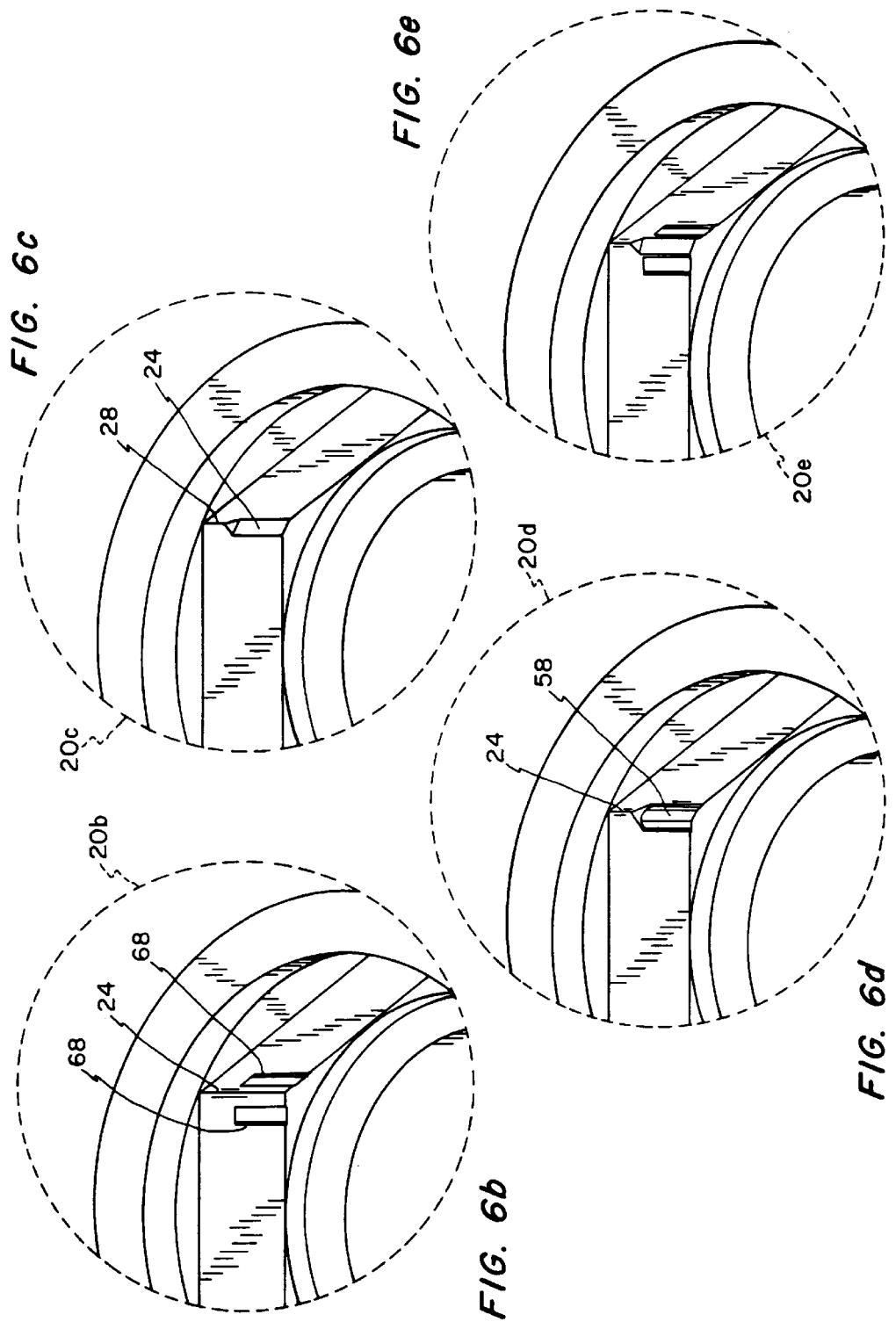

ANTI-ROTATIONAL CONNECTING MECHANISM

CROSS REFERENCE TO RELATED APPLICATIONS

This application is a continuation-in-part of U.S. application Ser. No. 08/451,083, filed on May 25, 1995, now U.S. Pat. No. 5,725,375, which claims the benefit of U.S. Provisional Patent Application No 60/002,741, filed on Aug. 24, 1995.

FIELD OF THE INVENTION

This invention relates to rotation-limiting connecting mechanisms of the kind employing a non-round post engaged in a non-round socket to connect two parts endwise in a fashion that limits relative rotation between the parts around their common longitudinal axis as embodied, for example, in a dental implant and an abutment, artificial tooth, or another article designed and intended for non-rotational, detachable connection to that implant.

BACKGROUND OF THE INVENTION

In dental implantology as currently being practiced it is common to use rotation-limiting connecting mechanisms consisting, for example, of a hexagonal post or socket on an implant and a mating socket or post on an article intended to be attached to the implant. There being a wide variety of such articles (posts, copings, artificial teeth, etc.), it is the prevailing manufacturing practice to employ standard sizes of such posts and sockets so that all such articles will fit interchangeably on all available implants of a given manufacturer. The dimensions being used are small. Owing in part to the limitations of manufacturing tolerances, the sockets are a little larger across than the posts in order to assure that in every case the dentist will be able to put two parts together at chairside, and when necessary to take them apart without difficulty. Typically, the distance between opposing flat surfaces of a hexagonal post may be about 0.0005 inch smaller than the distance between opposing flat surfaces of a mating hexagonal socket. While this arrangement provides an essential rotation-limiting connection, it leaves a small amount of rotational looseness which is undesirable in that it does not provide the stability of a natural tooth. More importantly, the rotational wiggling between parts creates an environment in which the screw that holds an article fixed to an implant can work itself loose. It is critically important to a successful dental restoration on an implant that the restoration not come loose on the implant.

GENERAL NATURE OF THE INVENTION

Generally, in accordance with the invention, a non-round post is detachably connected to a non-round socket in a manner which limits the relative rotation between the post and socket. As in the prior art, the ends of the post and socket have opposing flat surfaces which are spaced apart slightly to facilitate initial insertion of the post into the socket. Upon further insertion of the post into the socket, however, means are provided on the post, socket, or both to more tightly engage the parts and reduce the relative rotation between them. In one embodiment of the invention, a socket has internal means adjacent its bottom for engaging a prior art post more snugly at its free end. In another embodiment of the invention, a post has external means near its base for engaging a prior art socket more snugly near its opening. In a third embodiment of the invention, both a socket and post are provided with internal means and external means, respectively, for tightly engaging with each other in a manner which greatly reduces the relative rotation between them. In either embodiment, it is found that when two parts bearing the post and socket are fastened together, relative rotation of the parts around their common axis is substantially eliminated, thus forming a true anti-rotational connection.

As practiced in the customary hexagonal post and socket fittings used in implant dentistry, the socket in the first and third embodiments may have a hexagonal configuration with six discrete contact members arrayed one each in the corners between adjacent flat walls which contact the post at each of its corresponding corners, whereas in the second and third embodiments the post may have contact means adjacent its base which contact the socket in each of its corners. When, for example, an abutment fitted with the improved socket according to the first embodiment is fastened to the hexagonal post of an implant with the usual abutment screw, little or no relative rotation between the abutment and the implant around their common axis is detected. Similar results are possible when an improved post according to the second embodiment is fitted into a hexagonal socket of an implant, for example, and fastened to the implant with an appropriate screw, or where an improved post and improved socket according to the third embodiment are fitted together and fastened with an abutment screw.

BRIEF DESCRIPTION OF THE DRAWINGS

FIG. 1 is a perspective view of a typical prior-art rotation-limiting external "hex" post in common use on cylindrical dental implants having a threaded internal bore opening through the hex;

FIG. 2a schematically illustrates the prior art hex post and socket interlock;

FIG. 2b schematically illustrates the rotational looseness of the prior art interlock;

FIGS. 6a–6f are fragmentary perspective views of additional embodiments of sockets according to the invention;

DETAILED DESCRIPTION OF THE PREFERRED EMBODIMENTS

Figure 4:
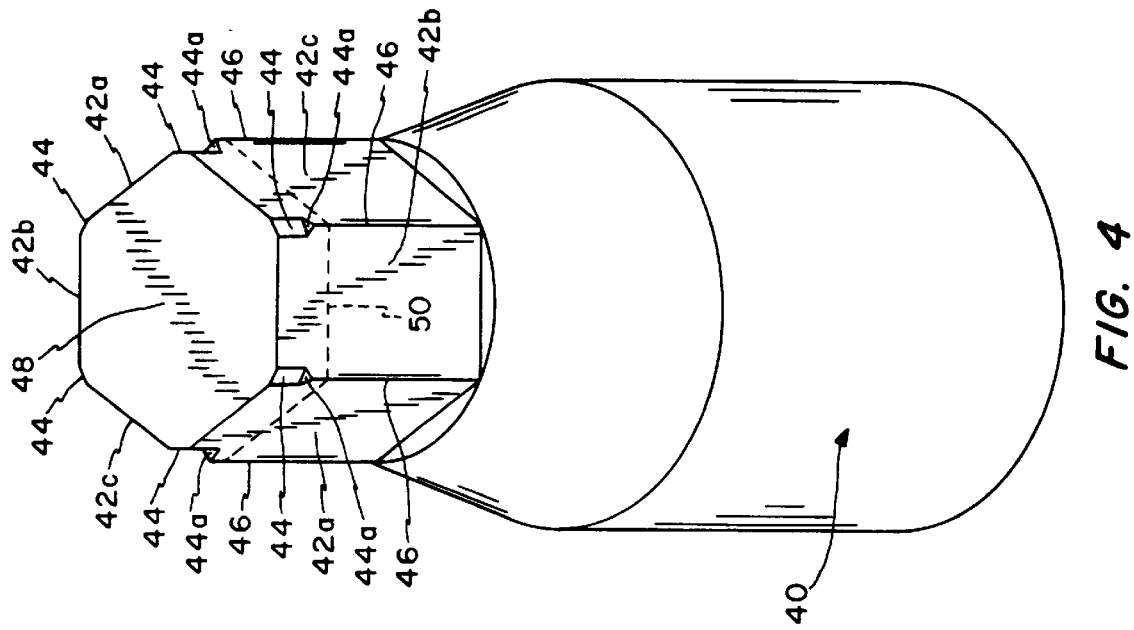
FIG. 4 is a perspective view of a new broach according to the invention for use in making the socket shown in FIG. 3.

FIG. 1 represents a prior art cylindrical dental implant 10 having a hex post 12 extending upwardly from its gingival surface 14. This structure is well-known and extensively used in dental implantology for single-tooth restorations, where it is important that the restored tooth not be free to pivot around the common longitudinal axis of the implant and the restoration. As is common practice at the present time, the hex post 12 has three pairs of opposite parallel flat surfaces 12a, 12b and 12c. These pairs of parallel surfaces may be achieved by straddle-milling an initially cylindrical post 12, leaving a thin round base portion 16 of the initial cylindrical post between the hex and the gingival surface 14. The locus of the initial cylinder remains also in the corner portions 16a–f, inclusive, between adjacent ends of the flat surfaces. A threaded bore 18 in the implant opens through the hex post.

FIG. 2a shows, in outline, the hex post of FIG. 1 inside a hexagonal socket. The socket has three pairs of opposite parallel walls 22a, 22b and 22c, adjacent ones of which meet in sharp corners 24. Each of these corners confronts one of the rounded corners 16 a–f of the post 12. The gap distance in each corner is larger than the distance "d" between confronting flat walls, as is shown in the figure, illustrating the rotational looseness of prior art hex post and socket connectors. The consequence of this looseness is illustrated in FIG. 2b, where the angle "a" is the angle through which the post can be turned in one direction or the other in the socket. The extent of looseness is, then, twice the angle "a". The magnitude of the angle "a" depends on the magnitude of the distance "d". In practice, prior art connectors may allow rotational looseness in the range between about 0.75 and 2 or more degrees in each direction. Such looseness can contribute to the loosening, over time, of the screws that are used to fasten dental restorations to dental implants.

Figure 3:
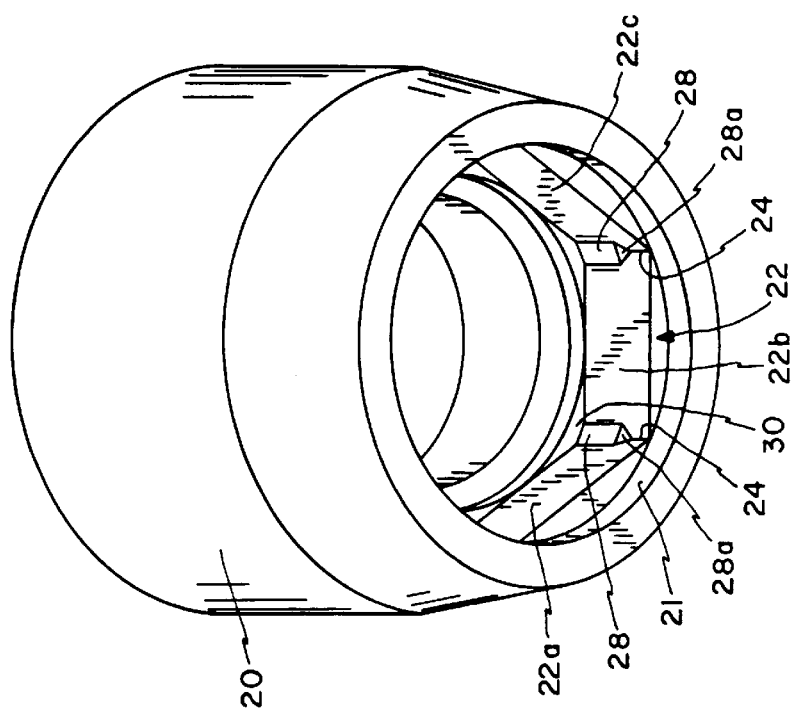
FIG. 3 is a perspective view of a component having an internal "hex" socket according to one embodiment of the invention designed for mating with the prior-art post of FIG. 1.

In FIG. 3 a component 20 of generally tubular shape has a hexagonal socket 22 sized for mating with the hex post 12. This socket, accordingly, has three pairs of opposite parallel flat surfaces 22a, 22b and 22c, as is illustrated in FIG. 2a. It is common practice to make the hexagonal sockets with a broach having sharp edges, which leaves the sharp corners 24 where adjacent flat walls 22a and 22b, or 22b and 22c, meet. In the embodiment of the invention shown in FIG. 3, the corner spaces in the socket 22 are partially filled with corner blocks 28 located one in each corner within the socket near the bottom 30 of the socket. This socket 22 may be formed with a broach 40 shown in FIG. 4. This broach has a tool portion end 48 extending back from which are three pairs of opposite parallel flat surfaces 42a, 42b and 42c, adjacent ones of which meet in sharp corners 46 corresponding respectively to the corners 24 in the socket 22. The tool portion that is used to form the socket is marked by a dashed line 50. The sharp corners 46 of this tool portion are each relieved from the end 48 part way to the line 50 by a longitudinally oriented flat surface 44 followed by a sloped surface 44a of generally triangular shape, the apex of which joins the sharp corner 46. This broach may be used to form the socket 22 with the corner blocks 28 wherein the sloping triangular surfaces 28a corresponds to the sloped surfaces 44a of the broach. When the component 20 is joined to the implant 10, the corner blocks 28 fill the gaps 26 (FIG. 2a) and grip the hex post 12 at its rounded corners 16a–f, inclusive, substantially eliminating rotational looseness. The sloping surfaces 28a facilitate a smooth entrance of the hex post into the restricted region of the socket occupied by the blocks 28.

Figure 5:
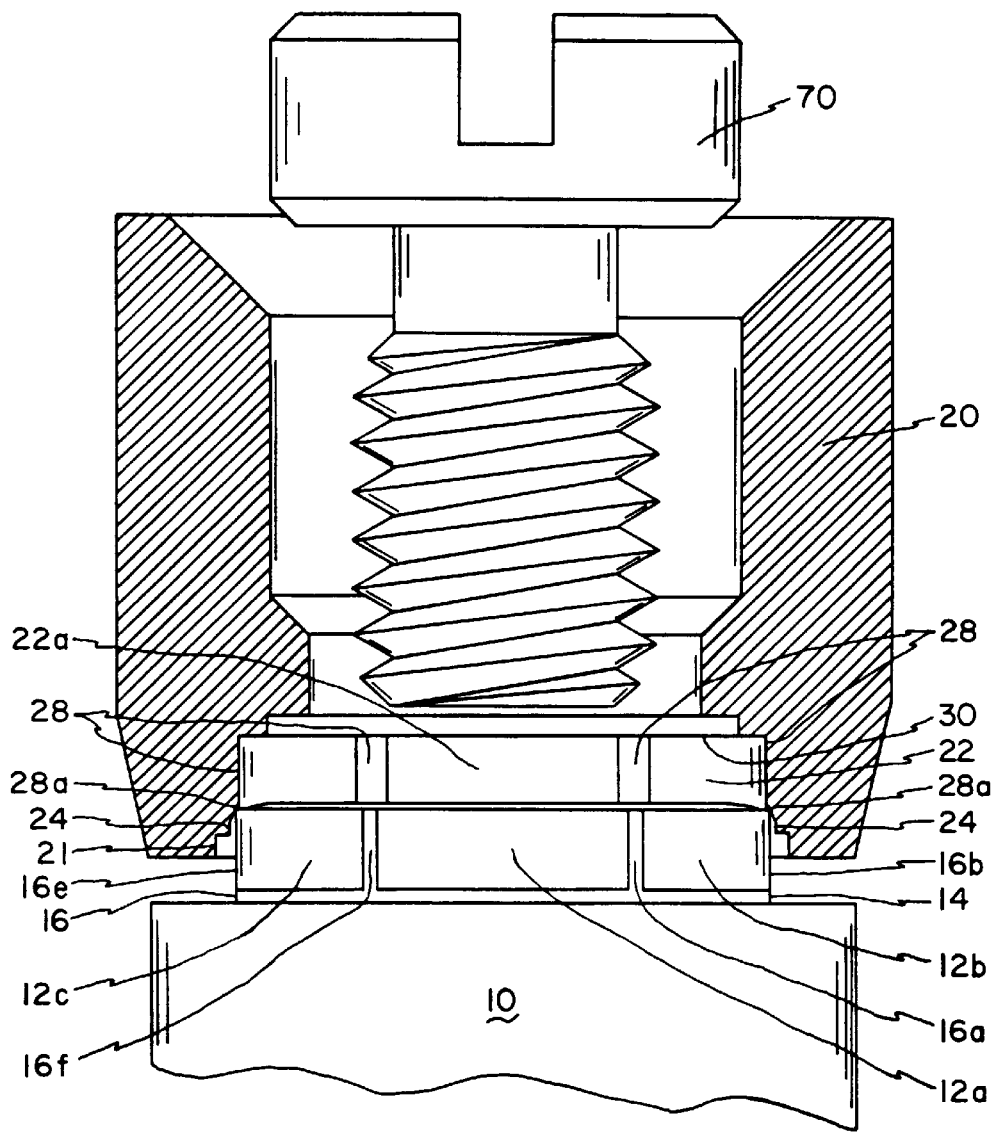
FIG. 5 is an enlarged side elevation, partially in section, of the socket of FIG. 3 being mated to the post of FIG. 1.

FIG. 5 shows how the component 20 and the implant 10 are joined via the hex post 12 and the hex socket 22. Referring to the ring 21, the corners 24, the sloped surfaces 28a and the blocks 28 of the component 20 which are shown in section on both sides of the post 12, the ring 21 (shown also in FIG. 3) is a prior-art feature to make room for the round base portion 16 of the hex post 12 when the component is seated on the implant surface 14. This ring is followed by the sharp corner portion 24 of the socket which, it will be observed, is spaced away from the hex post 12. This sharp corner portion is followed in turn by the sloped surface 28a of the corner block 28, making a gradual transition from the sharp spaced-away corner to contact between the hex post and the socket. Finally, the block 28 itself comes into firm contact with the hex post at each of the rounded corners 16a–f. The corner blocks can be dimensioned so that opposite pairs of the blocks 28 will squeeze the hex post between them at the corners 16a–f, inclusive. The component can be fastened to the implant with a usual abutment screw 70, for example.

FIG. 6a shows a modification of the component 20 in which corner shims 68, shown enlarged in a balloon 20a, are substituted for the corner blocks 28 shown in FIG. 3. The shims 68 make contact with sidewalls of a post near a corner to prevent rotation of the post in the socket, and rely less on squeezing the post between opposing blocks. These shims can be removed somewhat from the corners 24, as is shown in balloon 20b in FIG. 6b. The corner block 28 is shown in balloon 20c (FIG. 6c) for ready comparison. FIG. 6d shows a modified corner block 58 in balloon 20d, designed to combine the side contact of shims 68 with some squeezing effect of the blocks 28. FIG. 6e shows in balloon 20e a corner block 28 accompanied by side shims 68, illustrating still another embodiment of the anti-rotation socket of the invention.

Figure 6F:
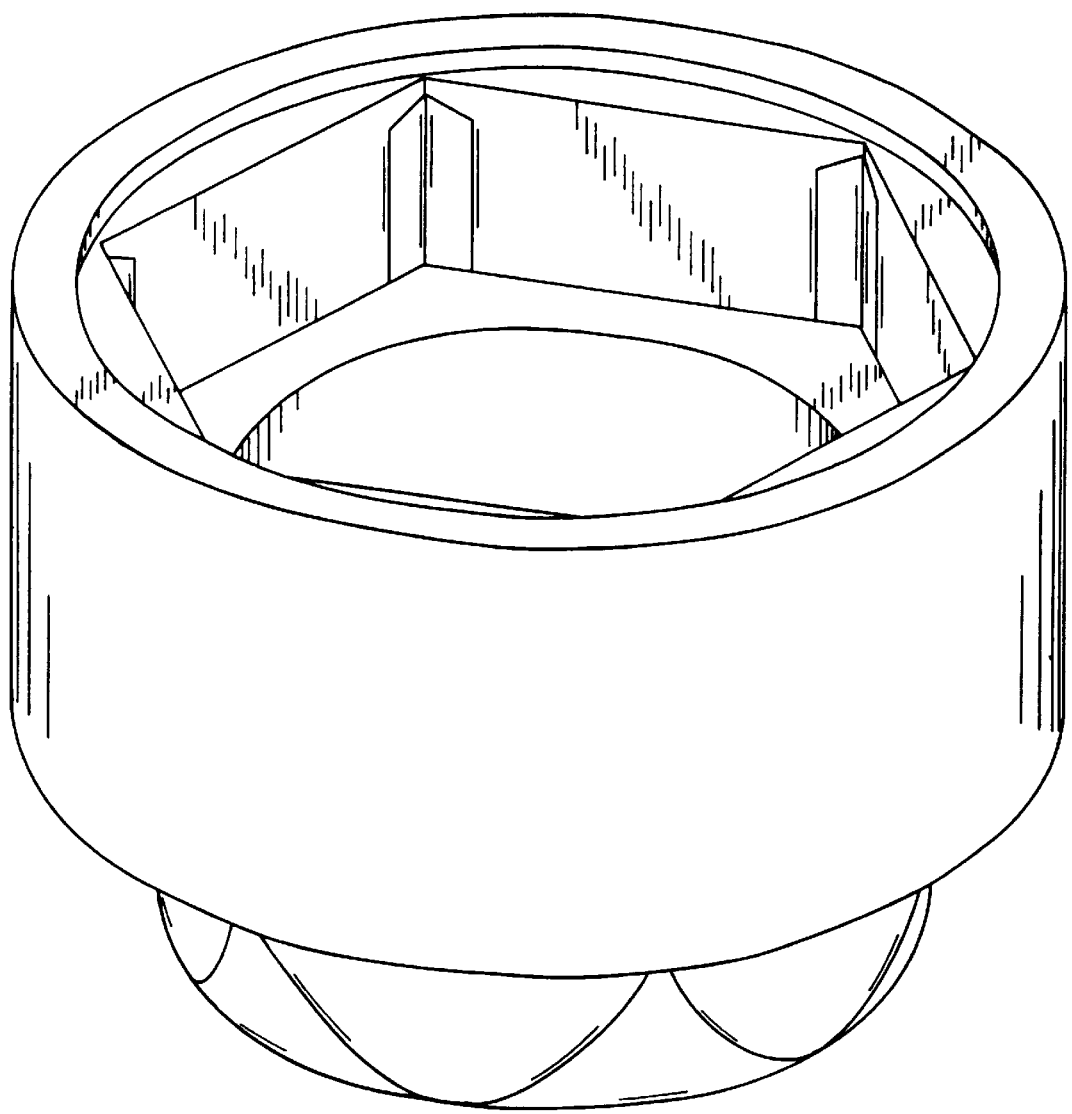

FIG. 6f shows a preferred embodiment of the invention which includes modified corner shims to facilitate a smooth entrance of the hex post into the socket while still providing an anti-rotational effect. The improvement can best be observed by comparing the shims shown in FIG. 6f to those shown in FIG. 6a. Referring to FIG. 6a, it is noted that the corner shims 68 have upper edges which are substantially parallel to and spaced below the upper edge of the socket. Upon initial insertion and until encountering the upper edge of the corner shims 68, the hex post fits within the socket with the same degree of rotational looseness as encountered in the prior art. As the post is inserted further into the socket, it encounters an abrupt "tightening" of fit along the upper edge of the corner shims 68. The embodiment shown in FIG. 6f facilitates entry of the post into the socket by angling the upper edges of each corner shim pair relative to the upper edge of the socket. Specifically, the top edges of each shim pair are angled toward each other and toward the upper edge of the socket so that they meet at an apex near the upper end of a corner of the socket. As the post is inserted into the socket, it initially encounters the same degree of rotational looseness as in the prior art, but quickly reaches the apexes of the angled shim pairs. As the post penetrates further into the socket, the sidewalls of the post contact the ends of the angled upper edges of the shims nearest the corners of the socket. Then, as the post is further inserted into the socket, the sidewalls gradually come into contact with progressively increasing surface areas of the shims until the shims are in full contact with the post and achieve the full anti-rotational effect. It may be noted that while the improvement of FIG. 6f has been described in relation to FIG. 6a, the same type of improvement may be achieved by angling the upper edges of the shims in other embodiments such as those shown in FIGS. 6b, 6d, and 6e.

Figure 7A:
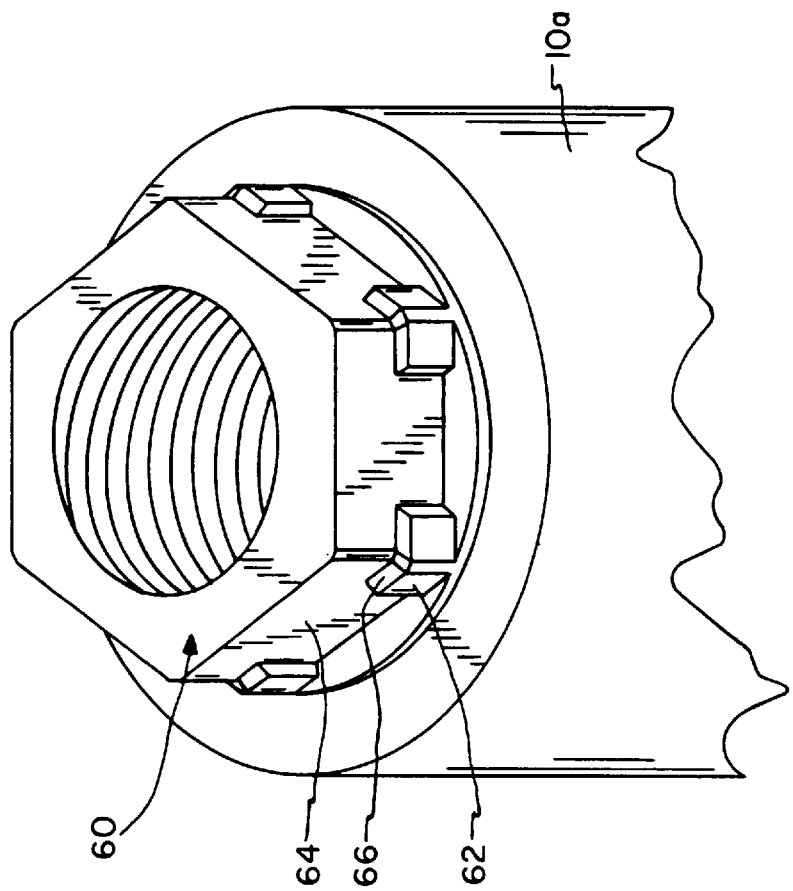
FIG. 7a is a perspective view of a post modified according to one embodiment of the invention.

The embodiments of the invention heretofore illustrated and described may be used with conventional hexagonal abutment posts existing in the prior art. In other embodiments of the invention, abutment posts are modified for use with conventional hexagonal sockets existing in the prior art. FIG. 7a illustrates, by way of example, an implant 10a having a hex post 60 modified according to one embodiment of the invention. The base portion 62 of this post is made large enough to fit snugly within a typical hex socket as found in abutments and other components designed for attachment to dental implant and dental analogs. This base portion 62 extends only a short distance from the base of the post 60 toward its free end. The end portion 64 is relieved by removing material from the corners of the hexagonal shape. An intermediate portion 66 provides a sloping transition from the base portion 62 to the end portion 64. The end portion 64 fits loosely within available hex sockets. Thus, when the post of the invention is pushed into a hex socket, it will enter easily until the intermediate portion 66 is reached, when slight additional force will be required to seat the post in the socket, with the base portion 62 engaging the walls of the socket. The required force will be supplied by the screw that is normally used to attach the mating parts to each other. This might be an abutment screw, or a screw or bolt used to mount a transfer coping on an implant or an implant analog, for example. These items being well known, they are not illustrated or described here.

Figure 7B:
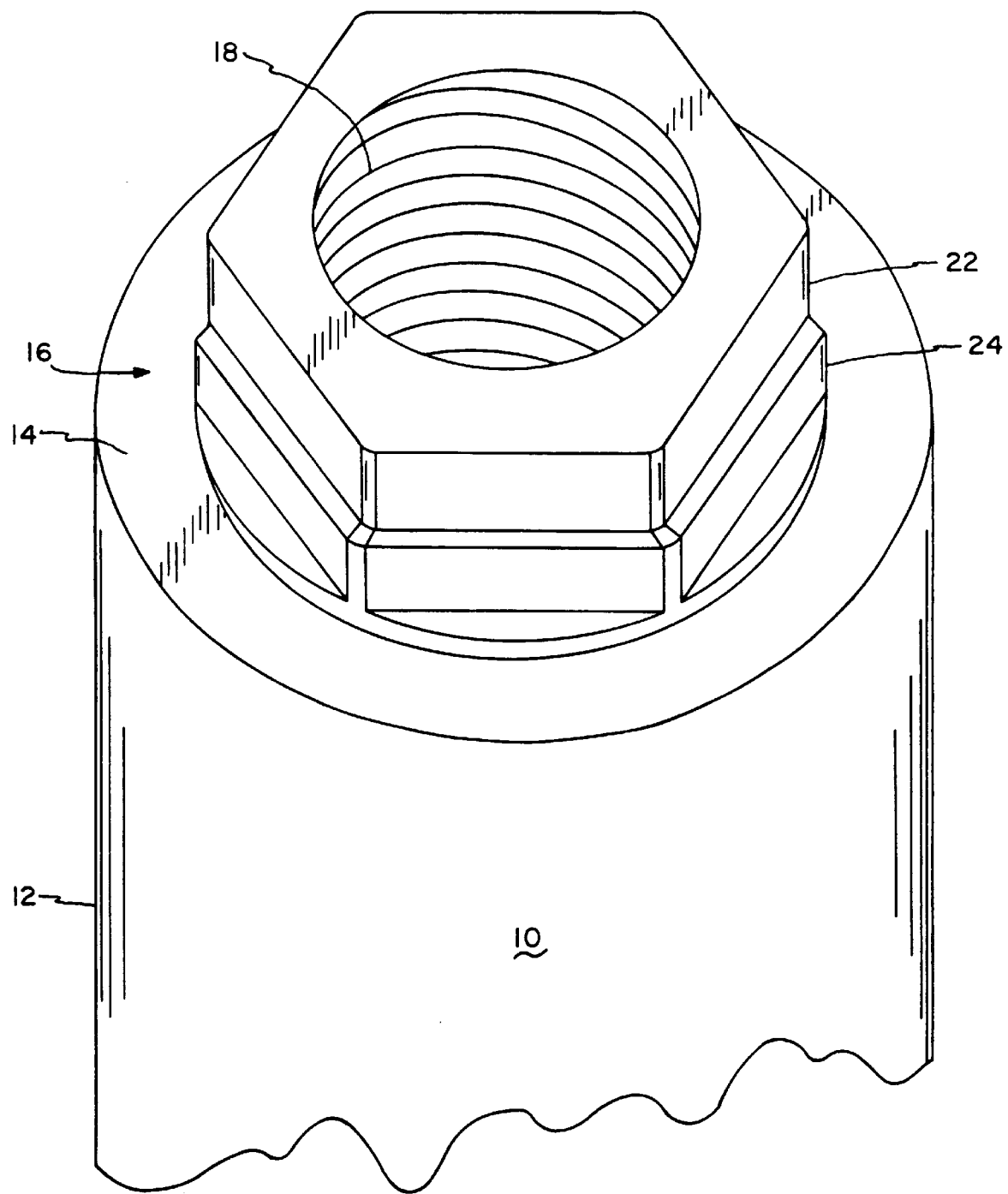
FIG. 7b illustrates a hex post having sections of different width which may be used to make the post of FIG. 7A.

The post 60 of the embodiment shown in FIG. 7a may be derived from the post 16 of FIG. 7b, which has a first section 22 remote from the gingival surface 14, on which the distance between flats is the normal distance as used in the prior art, and a second section 24 nearer to the gingival surface, on which the distance between flats is selected to be nearer to or the same as the larger distance between internal flats of the socket into which the post is intended to be fitted. The post as shown in FIG. 7b can be made by the well-known process of straddle-milling, but in two passes, the first of which produces a post having the second section of 24 with the larger distance between flats, and the second of which produces the first section 22 with the smaller distance between flats. This post can be guided into its mating socket with the same ease as a prior-art post, but it fits more tightly and minimizes freedom of relative rotation between parts when the second section 24 enters the socket.

Figure 7C:
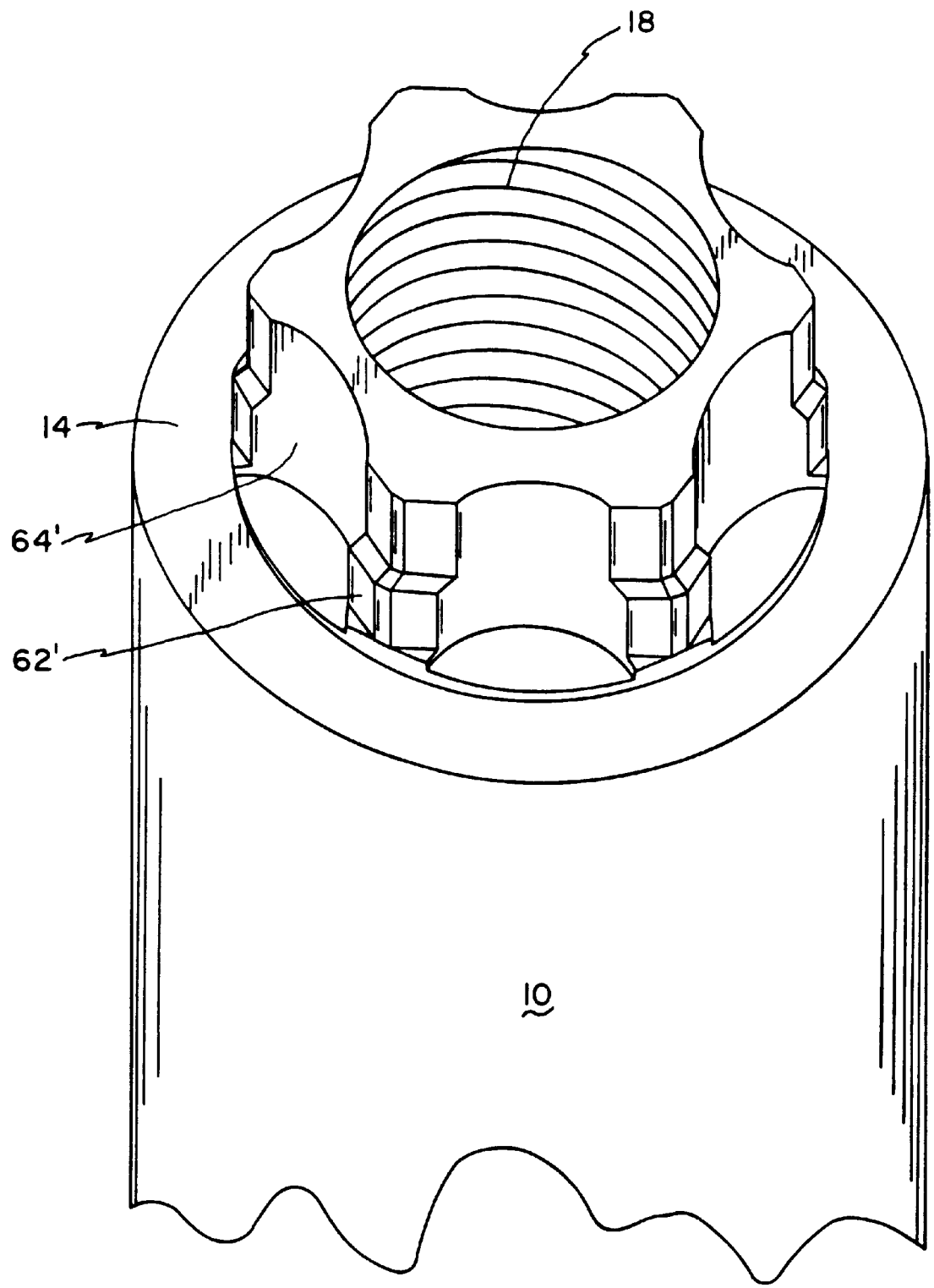
FIG. 7c shows a hex post made according to another embodiment of the invention.

FIG. 7c shows a further embodiment of the invention which may be derived from the post shown in FIG. 7a by performing a further milling step in which the straddle-milling tool is moved axially toward the gingival surface 14, to cut arcuate segments 64' in the sidewalls of the starting post shown in FIG. 7a, leaving the corner segments 62' substantially as shown in FIG. 7a. These arcuate segments can be cut to a depth to remove material from both sections 62 and 64 of the post, as is shown in FIG. 7c. Alternatively, the arcuate segments can be cut shallower so that material is removed only from the wider section 64. In either case, the embodiment of FIG. 7c reduces friction between the mating parts without compromising the anti-rotational feature of the invention.

Figure 8:
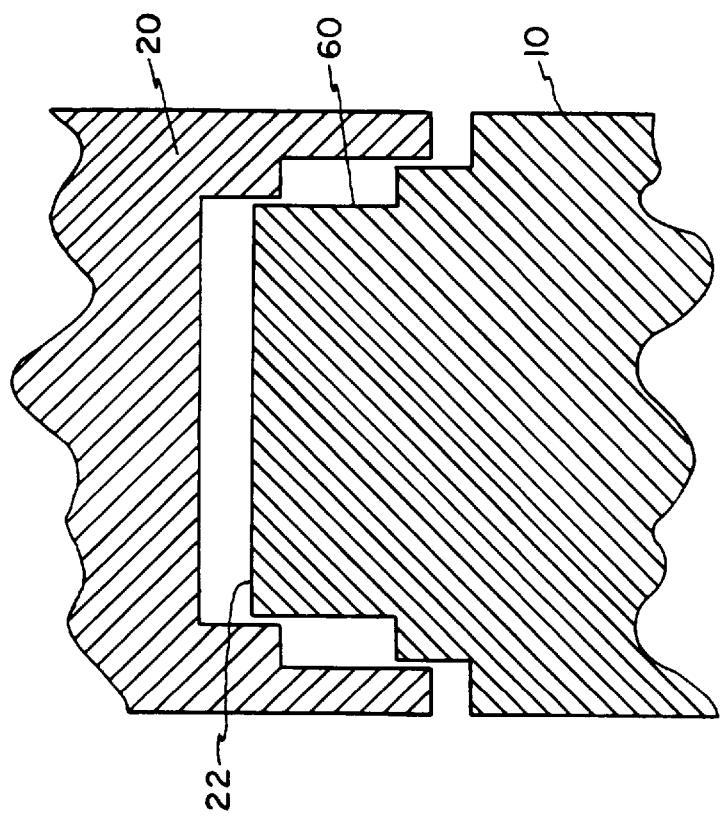
FIG. 8 is a vertical section of a post and socket according to one embodiment of the invention.

FIG. 8 shows how a post 62 of the invention may be combined with a socket 22 of the invention to provide a connecting mechanism in which each of the two parts embodies the improvement of the invention. As in other embodiments illustrated herein the post freely enters the socket, initially, and then is engaged more tightly when the post is fully seated in the socket.

While the invention has been illustrated in connection with posts and sockets which are currently in use in the field of dental implants, these illustrations are exemplary only. The scope of the invention is defined in the appended claims.

I claim:

1. A dental implant system comprising an implant and an abutment having an interlocking post and a socket, in which said post extends outwardly along a longitudinal axis from a base of said implant to a free end of said implant and said socket is a recess in said abutment extending inwardly from an outer end of said abutment to a base within said abutment, said post comprising a plurality of rigid and generally flat external sidewalls parallel to said longitudinal axis and meeting at corners, said socket comprising a corresponding plurality of generally flat internal sidewalls parallel to said longitudinal axis and meeting in corners, the improvement wherein said post and said socket are dimensioned so that said post fits loosely into said socket upon initial penetration and at least one of said post and socket has engagement means extending from its sidewalls so that said post fits progressively more tightly into said socket upon further penetration of said post into said socket and so that said post forms a substantially anti-rotational connection with said socket upon full penetration of said post into said socket.

2. A dental implant system according to claim 1 wherein said engagement means comprise a plurality of discrete engagement elements positioned non-continuously about the periphery of the sidewalls of at least one of said post and socket.

3. A dental implant system according to claim 2 in which said plurality of engagement elements are positioned in regions including said corners of said socket.

4. A dental implant system according to claim 2 in which said plurality of engagement elements are positioned in regions including said corners of said post.

5. The apparatus of claim 1 wherein said engagement means comprises a plurality of corner shim pairs positioned in the corners of at least one of said post and socket, each corner shim pair comprising a first and second corner shim having respective upper edges which are angled relative to an upper edge of said at least one of said post and socket to facilitate smooth entry of said post into said socket.

6. The dental implant system of claim 5 wherein said first and second corner shims intersect at the corners of said at least one of said post and socket, the respective upper edges of said first and second corner shims meeting at said corners to define an apex in each of said corners near the upper edge of said at least one of said post and socket.

7. A dental implant system comprising an implant and an abutment having an interlocking post and a socket, in which said post extends outwardly along a longitudinal axis from a base of said abutment to a free end of said abutment and said socket is a recess in said implant extending inwardly from an outer end of said implant to a base within said implant, said post comprising a plurality of rigid and generally flat external sidewalls parallel to said longitudinal axis and meeting at corners, said socket comprising a corresponding plurality of generally flat internal sidewalls parallel to said longitudinal axis and meeting in corners, the improvement wherein said post and said socket are dimensioned so that said post fits loosely into said socket upon initial penetration and at least one of said post and socket has engagement means extending from its sidewalls so that said post fits progressively more tightly into said socket upon further penetration of said post into said socket and so that said post forms a substantially anti-rotational connection with said socket upon full penetration of said post into said socket.

8. A dental implant system according to claim 7 wherein said engagement means comprise a plurality of discrete engagement elements positioned non-continuously about the periphery of the sidewalls of at least one of said post and socket.

9. A dental implant system according to claim 8 in which said plurality of engagement elements are positioned in regions including said corners of said socket.

10. A dental implant system according to claim 8 in which said plurality of engagement elements are positioned in regions including said corners of said post.

11. A dental implant system comprising an implant and an abutment having interlocking elements forming a post and a socket, said post extending outwardly along a longitudinal axis from a base of said implant to a free end of said implant and said socket extending inwardly from an outer end of said abutment to a base within said abutment, each of said interlocking elements forming a plurality of rigid and generally flat external sidewalls parallel to said longitudinal axis and meeting at corners, said socket comprising a corresponding plurality of generally flat internal sidewalls parallel to said longitudinal axis and meeting in corners, at least one of said interlocking elements having anti-rotation means projecting from its sidewalls toward the sidewalls of the other interlocking element and extending parallel to said longitudinal axis, said interlocking elements being dimensioned so that said post fits loosely into said socket upon initial penetration and then progressively more tightly to form an anti-rotational connection upon full penetration.

12. A dental implant system according to claim 11 wherein said anti-rotation means comprises a plurality of corner shim pairs positioned in corner regions of at least one of said post and socket, each of said corner regions including a corner and two adjoining sidewall regions extending from said corner a distance less than about half the distance to an adjacent corner.

13. A dental implant system according to claim 12 in which said corner shim pairs are positioned in corner regions of said socket, each of said corner shim pairs comprising a first and second corner shim having respective upper edges which are angled relative to an upper edge of said socket to facilitate smooth entry of said post into said socket.

14. The dental implant system of claim 13 wherein said first and second corner shims intersect at corners of said socket, the respective upper edges of said first and second corner shims meeting at said corners to define an apex in each of said corners near the upper edge of said socket.

15. A dental implant system according to claim 12 in which said corner shim pairs are positioned in said corner regions of said post, each corner shim pair comprising a first and second corner shim having respective upper edges which are angled relative to a leading edge of said post to facilitate smooth entry of said post into said socket.

16. The dental implant system of claim 15 wherein said first and second corner shims intersect at corners of said post, the respective upper edges of said first and second corner shims meeting at said corners to define an apex in each of said corners near the leading edge of said post.

17. A dental implant system according to claim 11 wherein said anti-rotation means comprises a plurality of corner shim pairs positioned in corner regions of at least one of said post and socket, each of said corner regions including a corner and two adjoining sidewall regions extending from said corner a distance less than about half the distance to an adjacent corner.

18. A dental implant system according to claim 17 in which said corner shim pairs are positioned in corner regions of said socket, each corner shim pair comprising a first and second corner shim having respective upper edges which are angled relative to an upper edge of said socket to facilitate smooth entry of said post into said socket.

19. The dental implant system of claim 18 wherein said first and second corner shims intersect at corners of said socket, the respective upper edges of said first and second corner shims meeting at said corners to define an apex in each of said corners near the upper edge of said socket.

20. A dental implant system according to claim 17 in which said corner shim pairs are positioned in said corner regions of said post, each corner shim pair comprising a first and second corner shim having respective upper edges which are angled relative to a leading edge of said post to facilitate smooth entry of said post into said socket.

21. The dental implant system of claim 20 wherein said first and second corner shims intersect at corners of said post, the respective upper edges of said first and second corner shims meeting at said corners to define an apex in each of said corners near the leading edge of said post.

22. A dental implant system comprising an implant and an abutment having interlocking elements forming a post and a socket, said post extending outwardly along a longitudinal axis from a base of said abutment to a free end of said abutment and said socket extending inwardly from an outer end of said implant to a base within said implant, said post forming a plurality of rigid and generally flat external sidewalls parallel to said longitudinal axis and meeting at corners, said socket comprising a corresponding plurality of generally flat internal sidewalls parallel to said longitudinal axis and meeting in corners, at least one of said interlocking elements having anti-rotation means projecting from its sidewalls toward the sidewalls of the other interlocking element and extending parallel to said longitudinal axis, said anti-rotation means being dimensioned so that said post fits loosely into said socket upon initial penetration and then progressively more tightly to form an anti-rotational connection upon full penetration.

23. A set of dental implant components adapted for anti-rotational connection comprising:

a first component aligned along a longitudinal axis and forming a socket having a base and an open end, the socket including a plurality of internal sidewalls parallel to said longitudinal axis and meeting at corners; and a second component aligned along said longitudinal axis and forming a post having a base and a free end, the post including a plurality of external sidewalls parallel to said longitudinal axis and meeting at corners, the free end of said post being adapted to penetrate partly into said socket to form an initial connection between said first part and said second part, said initial connection being loose enough to permit a small degree of relative rotation between said post and said socket, wherein engagement means are disposed on at least one of said first and second dental components for providing a progressively tightening connection between said first and second components upon further penetration of said post into said socket and a final connection between said first and second components upon full insertion of said post into said socket, said final connection being tighter than said initial connection and substantially eliminating the relative rotation between said post and said socket.

24. The set of components according to claim 23 in which said post and said socket have complimentary cross-sectional shapes.

25. The set of components according to claim 23 in which said post and said socket have polygonal cross-sectional shapes.

26. The set of components according to claim 23 in which said post and said socket have hexagonal cross-sectional shapes.

27. The set of components of claim 26 wherein one of said first and second components is a dental implant and the other of said first and second components is a dental abutment.

28. The set of components of claim 27 wherein said engagement means is located in the corners of at least one of said post and said socket.

* * * * *